(12) United States Patent
Schexnaider et al.

(10) Patent No.: US 8,997,562 B2
(45) Date of Patent: Apr. 7, 2015

(54) DRILLING FLUID SAMPLING SYSTEM AND SAMPLING HEAT EXCHANGER

(71) Applicant: Halliburton Energy Services, Inc., Houston, TX (US)

(72) Inventors: Neil Patrick Schexnaider, Rayne, LA (US); Matthew Hay Henderson, Inverbervie (GB)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 14/125,642

(22) PCT Filed: Jan. 21, 2013

(86) PCT No.: PCT/US2013/022400
§ 371 (c)(1),
(2) Date: Dec. 12, 2013

(87) PCT Pub. No.: WO2014/113037
PCT Pub. Date: Jul. 24, 2014

(65) Prior Publication Data
US 2014/0298899 A1    Oct. 9, 2014

(51) Int. Cl.
*E21B 49/00*      (2006.01)
*G01N 33/28*      (2006.01)
*E21B 49/08*      (2006.01)
*E21B 36/00*      (2006.01)

(52) U.S. Cl.
CPC ............ *G01N 33/2823* (2013.01); *E21B 49/08* (2013.01); *E21B 36/00* (2013.01); *E21B 49/005* (2013.01)

(58) Field of Classification Search
CPC ....... E21B 49/005; E21B 36/00; F28D 15/00; G01N 33/2823
USPC ............... 73/152.04, 152.19, 153.23, 863.11, 73/863.12; 175/17
See application file for complete search history.

(56) References Cited

U.S. PATENT DOCUMENTS 2,408,964 A * 10/1946 Winn et al. ...................... 436/30
3,240,068 A *  3/1966 Horeth et al. ............... 73/863.12
(Continued)

FOREIGN PATENT DOCUMENTS

CA          2377424 A1    9/2003
WO    2006/022735 A1    3/2006
(Continued)

OTHER PUBLICATIONS

PCT/US2013/022400 International Search Report and Written Opinion Dated Oct. 10, 2013 (13 p.).

*Primary Examiner* — John Fitzgerald (57) ABSTRACT

A system for sampling drilling fluid to identify one or more species of interest within the drilling fluid includes a heat exchanger. The heat exchanger has a first fluid passage and a second fluid passage. Each fluid passage has an inlet and an outlet. In addition, the system includes a supply line coupled to the inlet of the first fluid passage. Further, the system includes a return line coupled to the outlet of the second fluid passage. Still further, the system includes a drilling fluid heater having an inlet coupled to the outlet of the first fluid passage and an outlet. The system also includes a drilling fluid degasser having an inlet coupled to the outlet of the heater, a first outlet coupled to an analyzer configured to identify the one or more species of interest, and a second outlet coupled to the inlet of the second fluid passage.

17 Claims, 5 Drawing Sheets

(56) References Cited

U.S. PATENT DOCUMENTS

| | | | |
|---|---|---|---|
| 3,381,536 A * | 5/1968 | Horeth et al. | 73/863.12 |
| 3,713,499 A | 1/1973 | Arscott et al. | |
| 4,134,462 A | 1/1979 | Clay | |
| 4,215,753 A | 8/1980 | Champness | |
| 4,294,593 A * | 10/1981 | Rehm | 96/160 |
| 4,324,299 A * | 4/1982 | Nagel | 175/107 |
| 4,396,504 A | 8/1983 | Tannehill | |
| 4,501,143 A * | 2/1985 | Prior et al. | 73/152.19 |
| 4,510,800 A * | 4/1985 | Prior | 73/152.22 |
| 4,510,801 A * | 4/1985 | Quigley et al. | 73/152.19 |
| 4,565,086 A * | 1/1986 | Orr, Jr. | 73/19.09 |
| 4,813,270 A | 3/1989 | Baillie | |
| 4,869,810 A | 9/1989 | Ellingsen et al. | |
| 4,872,949 A | 10/1989 | Wilwerding | |
| 5,101,894 A | 4/1992 | Hendricks | |
| 6,443,001 B1 * | 9/2002 | Duriez et al. | 73/152.19 |
| 6,666,099 B2 * | 12/2003 | Taylor | 73/863.12 |
| 6,742,603 B2 * | 6/2004 | Polizzotti et al. | 175/17 |
| 6,779,606 B1 | 8/2004 | Lopez | |
| 7,819,205 B2 | 10/2010 | Tobben | |
| 7,891,426 B2 | 2/2011 | Williams | |
| 7,957,903 B1 * | 6/2011 | Selman et al. | 702/6 |
| 2002/0178842 A1 * | 12/2002 | Taylor | 73/863.12 |
| 2004/0154786 A1 | 8/2004 | Lach | |
| 2005/0034852 A1 | 2/2005 | Irwin, Jr. | |
| 2009/0184065 A1 | 7/2009 | Cremer | |
| 2013/0192360 A1 * | 8/2013 | Jamison et al. | 73/152.19 |
| 2013/0270006 A1 * | 10/2013 | Selman et al. | 175/24 |
| 2014/0202664 A1 * | 7/2014 | Schexnaider et al. | 165/104.19 |

FOREIGN PATENT DOCUMENTS

| | | |
|---|---|---|
| WO | 2011/073704 A2 | 6/2011 |
| WO | 2011/091626 A1 | 8/2011 |
| WO | 2011/092213 A2 | 8/2011 |

* cited by examiner

DRILLING FLUID SAMPLING SYSTEM AND SAMPLING HEAT EXCHANGER

CROSS-REFERENCE TO RELATED APPLICATIONS

This application is a 35 U.S.C. §371 national stage application of PCT/US2013/022400 filed Jan. 21, 2013, which is hereby incorporated herein by reference in its entirety for all purposes.

STATEMENT REGARDING FEDERALLY SPONSORED RESEARCH OR DEVELOPMENT

Not applicable.

BACKGROUND

1. Field of the Disclosure

The disclosure relates generally to drilling systems. More particularly, the disclosure relates to drilling fluid circulation and sampling systems for drilling operations.

2. Background of the Technology

To drill a borehole in the earth for the recovery of hydrocarbons (e.g., oil and gas), an earth-boring drill bit is mounted on the lower end of a tubular drill string and is rotated. With weight applied to the drill string, also referred to as weight-on-bit (WOB), the rotating drill bit engages the earthen formation and proceeds to form a borehole along a predetermined path toward a target zone. While the bit is rotated, drilling fluid is pumped from the surface through the drill string and directed out of nozzles in the face of the drill bit into the bottom of the borehole. The drilling fluid exiting the bit is forced from the bottom of the borehole to the surface through the annulus between the drill string and the borehole sidewall.

The drilling fluid, also referred to as drilling mud, performs several functions—maintains a desired pressure within the borehole, cools and lubricates the drill bit, carries rock cuttings to the surface, maintains borehole stability, and transmits hydraulic energy to downhole tools. For example, managing the pressure in the well is important to inhibit the influx of formation fluids into the wellbore, while ensuring excessive wellbore pressure does not fracture the formation and lead to significant drilling fluid loss into the formation. The drilling fluid returning to the surface via the annulus is processed and reconditioned to remove rock cuttings, sand and other solids, as well as to ensure proper mud weight and density, pH, etc. After such processing and reconditioning, the drilling fluid is temporarily stored in mud tanks at the surface, and then pumped back down the drillstring. In this manner, the drilling fluid is continuously recirculated through the drilling system.

As the drilling fluid is circulated through the drilling system, samples of the drilling fluid returning to the surface are continuously taken to identify species of interest (liquids and gases) in the drilling fluid. Typically, the species of interest in the returning drilling fluid to be identified and monitored include hydrocarbons (e.g., methane, ethane, propane, i-butane, n-butane, i-pentane, n-pentane, n-hexane, ethane, propene, etc.), carbon dioxide, hydrogen, helium, sulfur dioxide, benzene, and hydrogen sulfide. In particular, the drilling fluid samples are heated to volatize or vaporize any liquid species of interest in the drilling fluid. Typically, electric heaters are employed to heat the drilling fluid samples. Once volatized and separated from the drilling fluid, the species of interest are transported to analytical equipment for further processing and analysis. This process of removing species of interest from drilling fluid for analytical purposes is commonly referred to as "degassing" or "extracting," with the resulting gaseous samples being called "representative sample gas" as it is generally representative of the species of interest in the returned drilling fluid stream at that particular time. Once the species of interest are removed, the heated drilling fluid is returned to the drilling process. However, the thermal energy in the heated samples of drilling fluid may detrimentally impact the equipment (e.g., pumps) used to transport the drilling fluid back to the drilling process. Moreover, the hot samples of drilling fluid present a potential safety hazard to personnel positioned near the drilling fluid sample return line.

BRIEF DESCRIPTION OF THE DRAWINGS

For a detailed description of the preferred embodiments of the disclosure, reference will now be made to the accompanying drawings.

DETAILED DESCRIPTION OF THE PREFERRED EMBODIMENTS

The following discussion is directed to various exemplary embodiments. However, one skilled in the art will understand that the examples disclosed herein have broad application, and that the discussion of any embodiment is meant only to be exemplary of that embodiment, and not intended to suggest that the scope of the disclosure, including the claims, is limited to that embodiment.

Certain terms are used throughout the following description and claims to refer to particular features or components. As one skilled in the art will appreciate, different persons may refer to the same feature or component by different names. This document does not intend to distinguish between components or features that differ in name but not function. The drawing figures are not necessarily to scale. Certain features and components herein may be shown exaggerated in scale or in somewhat schematic form and some details of conventional elements may not be shown in interest of clarity and conciseness.

In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection, or through an indirect connection via other devices, components, and connections. In addition, as used herein, the terms "axial" and "axially" generally mean along or parallel to a central axis (e.g., central axis of a body or a port), while the terms "radial" and "radially" generally mean perpendicular to the central axis. For instance, an axial distance refers to a distance measured along or parallel to the central axis, and a radial distance means a distance measured perpendicular to the central axis.

Figure 1:
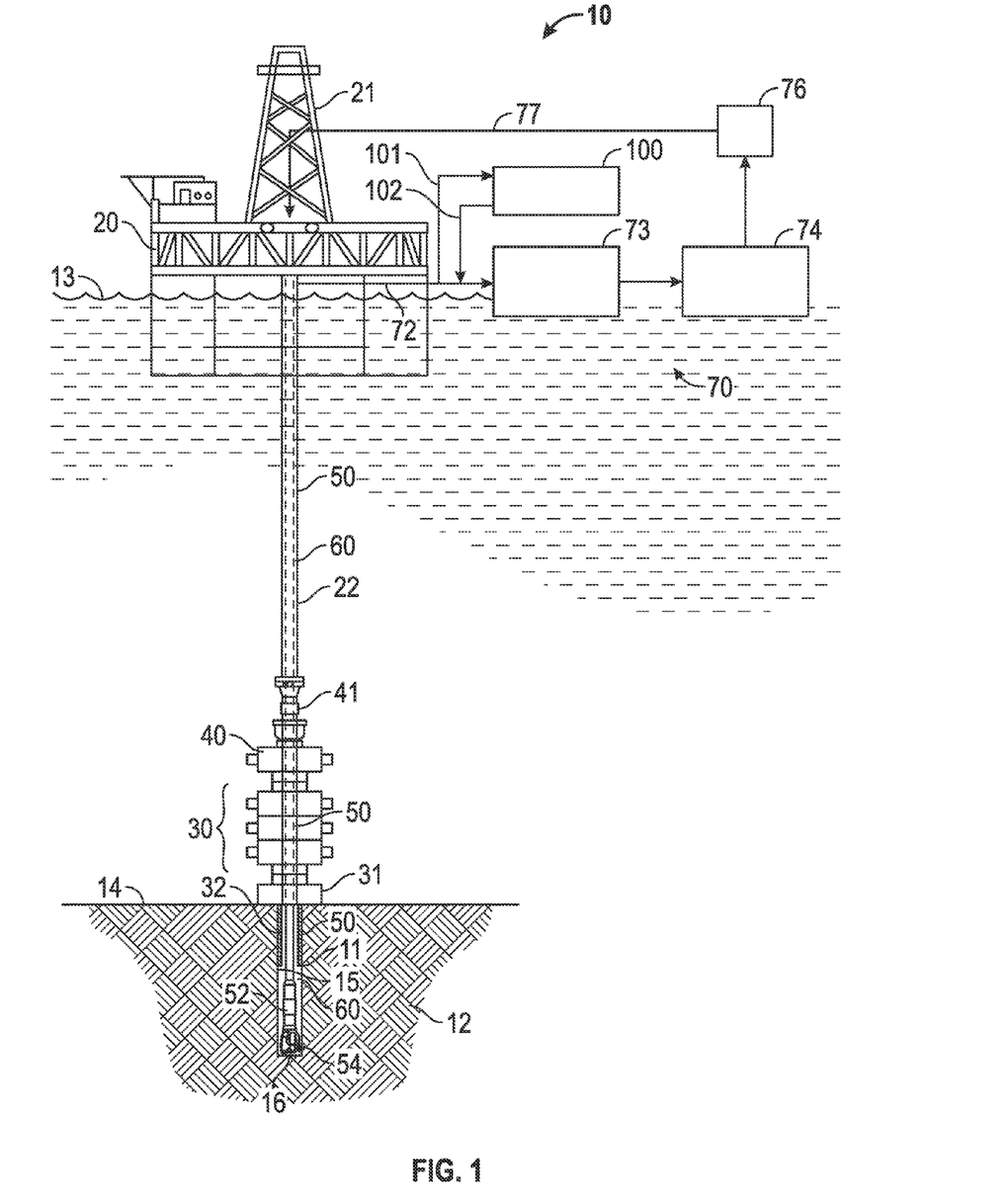
FIG. 1 is a schematic view of an embodiment of an offshore drilling system in accordance with the principles described herein.

Referring now to FIG. 1, an embodiment of an offshore drilling system 10 for drilling a subsea borehole 11 in an earthen formation 12 is shown. In this embodiment, system 10 includes an offshore platform 20 (e.g., a semi-submersible platform) disposed at the sea surface 13, a subsea blowout preventer (BOP) 30 mounted to a wellhead 31 at the sea floor 14, and a lower marine riser package (LMRP) 40 mounted to the upper end of BOP 30. The upper end of LMRP 40 comprises a riser flex joint 41 connected to the lower end of a drilling riser 22 extending from platform 20. As will be described in more detail below, riser 22 takes mud returns from borehole 11 to platform 20. Flex joint 41 allows riser 22 to deflect angularly relative to BOP 30 and LMRP 40 while hydrocarbon fluids flow from wellbore 11, BOP 30 and LMRP 40 into riser 22.

Platform 20 is equipped with a derrick 21 that supports a hoist (not shown). A drill string 50 suspended from derrick 21 extends from platform 20 through riser 22, LMRP 40, BOP 30, and into borehole 11. Drill string 50 includes a plurality of drill pipe joints coupled together end-to-end, a bottom-hole-assembly (BHA) 52 coupled to the lowermost pipe joint, and a drill bit 54 coupled to the lower end of BHA 52. During drilling operations, weigh-on-bit (WOB) is applied as drill bit 54 is rotated, thereby enabling drill bit 54 to engage formation 12 and drill borehole 11 along a predetermined path toward a target zone. In general, drill bit 54 may be rotated with drill string 50 from platform 20 with a top drive or rotary table, and/or with a downhole mud motor within BHA 52. Casing 32 is installed and cemented in an upper portion of borehole 11 extending downward from wellhead 31 at the sea floor 14.

An annular space or annulus 60 is disposed about drill-string 50 and extends from drill bit 54 to platform 20. Moving upward from drill bit 54, annulus 60 is radially positioned between the sidewall 15 of borehole 11 and drill string 50, between casing 32 and drill string 50, between BOP 30 and drill string 50, between LMRP 40 and drill string 50, and between riser 22 and drill string 50. In other words, annulus 60 extends through borehole 20, casing 32, BOP 30, LMRP 40, and riser 22.

Referring still to FIG. 1, a drilling fluid supply or circulation system 70 disposed on platform 20 processes, conditions, samples, and circulates a suitable drilling fluid, also referred to as mud or drilling mud, to cool drill bit 54, remove cuttings from the bottom 16 of borehole 11 and carry them to platform 20 through annulus 60, and maintain a desired pressure or pressure profile in borehole 11 during drilling operations. In this embodiment, drilling fluid supply system 70 includes a drilling fluid conditioning system 73, a drilling fluid reservoir or tank 74, and a drilling fluid supply or mud pump 76. A drilling fluid return line 72 couples conditioning system 73 to riser 22, and a drilling fluid supply line 77 couples mud pump 76 to the upper end of drill string 50. Thus, drilling fluid returning from borehole 11 through annulus 60 is supplied to system 70 via return line 72, and drilling fluid processed and conditioned by system 70 is supplied by system 70 to drill string 50 via supply line 77.

During drilling operations, drilling fluid from tank 74 is pressurized by pump 76 and sent through fluid supply line 77 into drill string 50. The drilling fluid flows down drill string 50 and is discharged at the borehole bottom 16 through nozzles in drill bit 54. The drilling fluid cools bit 54 and carries the formation cuttings to platform 20 through annulus 60. The drilling fluid returned to platform 20 via annulus 60 exits the upper end of riser 22 through return line 72 and flows into conditioning system 73, which effectively cleans and conditions the drilling fluid before it is circulated back into drill string 50. In particular, conditioning system 73 removes undesirable solids from the drilling fluid (e.g., formation cuttings) and removes undesirable gases from the drilling fluid (e.g., dissolved hydrocarbon gases). Such functions are performed in conditioning system 73 by equipment known in the art including, without limitation, shakers, desanders, desilters, degassers, mud cleaners, centrifuges, etc. The cleaned drilling fluid flows from conditioning system 73 into tank 74. The chemistry (e.g., pH, concentration of corrosion inhibiting chemicals, etc.) and density of the drilling fluid can be adjusted in conditioning system 73 or in tank 74. The cleaned and conditioned drilling fluid in tank 74 is then supplied by pump 76 back down drill string 50. In this manner, drilling fluid is continuously circulated through drilling system 10, cleaned, processed, and conditioned.

Referring still to FIG. 1, in this embodiment, drilling system 10 also includes a drilling fluid sampling system 100 disposed on a skid supported by platform 20. Sampling system 100 is in fluid communication with circulation system 70 and continuously samples and analyzes drilling fluid returning from annulus 60 to identify species of interest within the drilling fluid. In this embodiment, samples of drilling fluid are continuously taken by sampling system 100 from return line 72 via a sample supply line 101 positioned upstream of conditioning system 73, and analyzed samples of drilling fluid are continuously returned from sampling system to return line 72 via a sample return line 102 positioned upstream of conditioning system 73. Thus, sampling system 100 acquires unprocessed samples of drilling fluid returning from annulus 60, analyzes the unprocessed samples of drilling fluid, and then returns the analyzed samples of drilling fluid to return line 72 for subsequent processing by conditioning system 73. As noted above and will be described in more detail below, sampling system 100 analyzes samples of drilling fluid returned to the surface from annulus 60. However, it should be appreciated that a sampling system (e.g., sampling system 100) can also be provided to analyze samples of drilling fluid being pumped down the drill string (e.g., drill string 50). By analyzing samples of drilling fluid pumped downhole and returned from the borehole, a differential analysis of the species of interest identified, and quantities thereof, can be performed.

Figure 2:
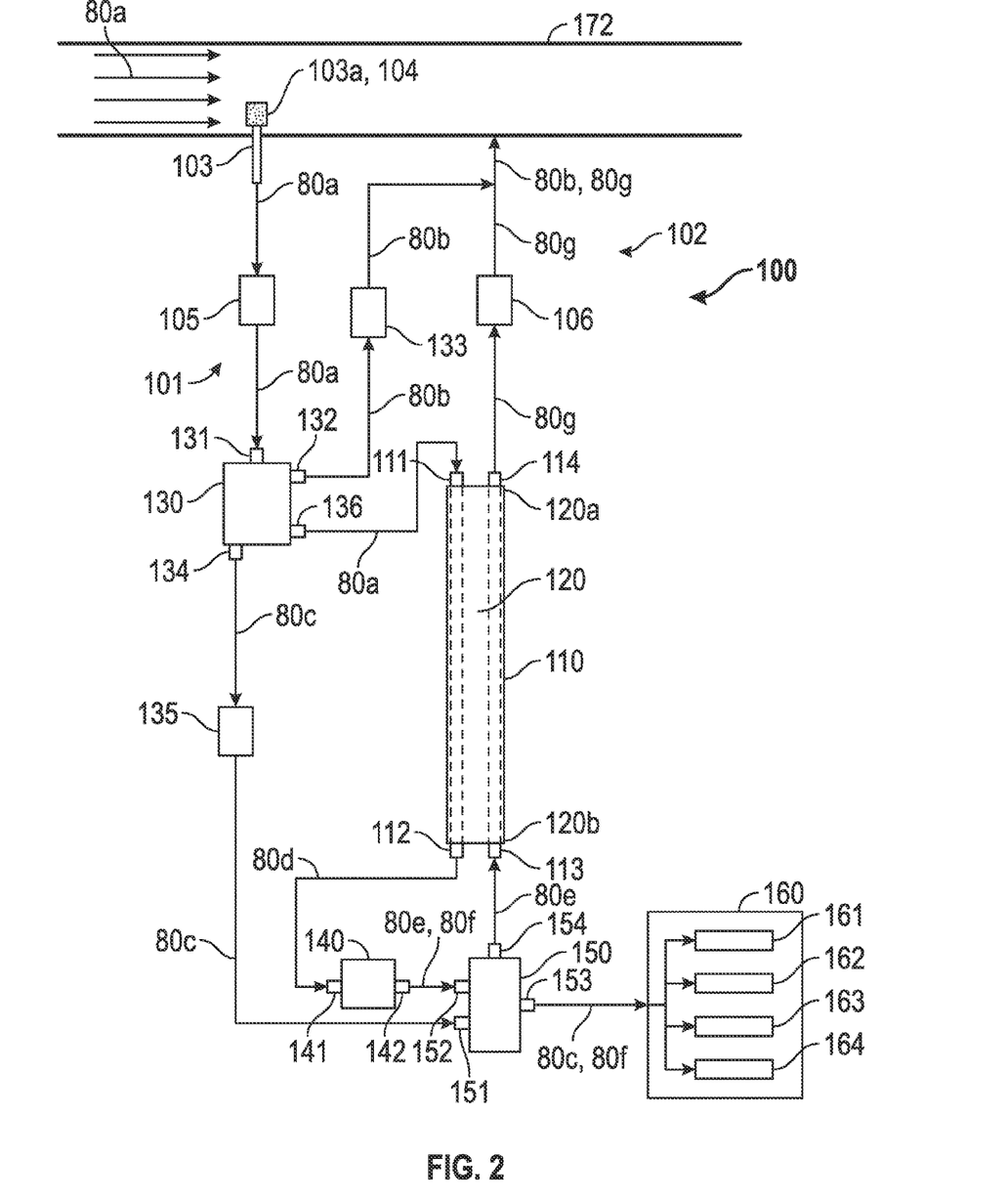
FIG. 2 is a schematic view of the drilling fluid sampling system of FIG. 1.

Referring now to FIG. 2, in this embodiment, sampling system 100 includes a heat exchanger 110, a phase separator 130, a heater 140, and a sample degasser 150. Supply line 101 continuously pulls samples of drilling fluid from return line 72 and flows the samples to phase separator 130. In this embodiment, supply line 101 includes a suction tube 103 extending through return line 72 and having an inlet end 103a disposed in the stream drilling fluid. The drilling fluid in return line 72 upstream of conditioning system 73 is unprocessed, and thus, contains formation cuttings and other undesirable solids. Thus, in this embodiment, a filter 104 is mounted to inlet end 103a to restrict solids from passing into sampling system 100. A sample supply pump 105 is provided in supply line 101 to pull drilling fluid samples from return line 72 and aid in continuously circulating samples of drilling fluid through system 100. The drilling fluid flowing through return line 72 and supply line 101 has not been heated, and thus, may be described as "cold" drilling fluid. For purposes of clarity and further explanation, the cold drilling fluid flowing through return line 72 and supply line 101 is designated with reference numeral 80a.

Cold drilling fluid 80a flows from supply line 101 into phase separator 130 through a drilling fluid inlet 131 and exits heat exchanger 110 through a drilling fluid outlet 112. Within phase separator 130, any solids in cold drilling fluid 80a (i.e., solids that passed through filter 104) are substantially separated from cold drilling fluid 80a and any gases entrained in the cold drilling fluid 80a (i.e., bubbles in drilling fluid 80a) are substantially separated. The separated solids, designated with reference numeral 80b, are carried by a small amount of cold drilling fluid 80a, exit phase separator 130 through a separated solids outlet 132, and are pumped to sample return line 102 and into drilling fluid return line 72 with a solids removal pump 133. The separated gases, designated with reference numeral 80c, are carried by a small amount of cold drilling fluid 80a, exit phase separator 130 through a separated gas outlet 134, and are pumped to degasser 150 with a de-aerator pump 135. Gases 80c may include relatively light hydrocarbons that are already in a gaseous state in cold drilling fluid 80a, and thus, are liberated therefrom with relative ease. In particular, cold drilling fluid 80a does not need to be heated to liberate gases 80c via volatilization or vaporization since they are already in a gaseous state. Following separation of solids 80b and gases 80c, the remaining cold drilling fluid 80a exits phase separator 130 through a separated drilling fluid outlet 136 and flows to heat exchanger 110.

In general, phase separator 130 can comprise any suitable device known in the art for separating solids (e.g., solids 80b) and entrained gases (e.g., gases 80c) from drilling fluid (e.g., cold drilling fluid 80a). In this embodiment, phase separator 130 is a de-aerator dampener separator (DDS) as developed by Halliburton Energy Services, Inc. of Houston, Tex. Examples of such de-aerator dampener separators are disclosed in PCT International Patent Application Publication No. WO/2011/014141. In addition, pumps 133, 135 may comprise any suitable pumps known in the art for pumping solid-liquid mixtures and gas-liquid mixtures, respectively. In this embodiment, both pumps 133, 135 are peristaltic pumps such as Bredel pumps available from Watson-Marlow Pumps Group of the UK, Delasco™ pumps available from PCM USA Inc. of Houston, Tex., and Masterflex® pumps available from Cole-Parmer North America of Vernon Hills, Ill.

Cold drilling fluid 80a, following separation of solids 80b and gases 80c, exits phase separator 130 through outlet 136 and flows into heat exchanger through an inlet 111. As will be described in more detail below, within heat exchanger 110, thermal energy is transferred to cold drilling fluid 80a thereby transitioning cold drilling fluid 80a into a pre-heated drilling fluid 80d. Accordingly, inlet 111 may also be referred to as cold drilling fluid inlet 111, and outlet 112 may also be referred to as pre-heated drilling fluid outlet 112.

Referring still to FIG. 2, pre-heated drilling fluid 80d exiting outlet 112 of heat exchanger 110 flows into heater 140 through inlet 141. Within heater 140, pre-heated drilling fluid 80d is further heated to a temperature sufficient to volatize and/or vaporize the species of interest therein. For most drilling operations, the pre-heated drilling fluid 80d is preferably heated to at least 70° C., and more preferably 80° C. The addition of thermal energy transforms pre-heated drilling fluid 80d into "hot" drilling fluid, designated with reference numeral 80e, and volatized and/or vaporized gaseous species of interest 80f, both of which exits heater 140 through outlet 142. In general, heater 140 can comprise any suitable heater known in the art for increasing the temperature of drilling fluid. In this embodiment, heater 140 is an electric heater.

Degasser 150 receives separated gases 80c (carried by a small amount of cold drilling fluid 80a and pumped by de-aerator pump 135) through a first inlet 151, and receives the mixture of hot drilling fluid 80e and gaseous species of interest 80f from heater 140 through a second inlet 152. Within degasser 150, gases 80c, hot drilling fluid 80e, and gaseous species of interest 80f are recombined, and then gases 80c, 80f are separated from hot drilling fluid 80e. The separated gases 80c, 80f exit degasser 150 through a gas outlet 153 and flow to an analyzer 160 that identifies the species of interest within gases 80c, 80f as described in more detail below. Collectively, gases 80c, 80f may be referred to as "representative sample gas" as they are generally representative of the species of interest in the returned drilling fluid stream at that particular time. The hot drilling fluid 80e exits degasser 150 through a hot drilling fluid outlet 154 and flows to heat exchanger 110.

In general, degasser 150 can comprise any suitable device known in the art for separating gases (e.g., gases 80c, 80f) from liquids (e.g., hot drilling fluid 80e). In this embodiment, degasser 150 is a hydro-cyclone degasser. Another example of a degasser that can be used as degasser 150 is the QGM Gas Trap available from Diversified Well Logging Inc. of Reserve, La.

As previously described, analyzer 160 receives separated gases 80c, 80f from gas outlet 153 of degasser 150. Within analyzer 160, the species of interest in gases 80c, 80f are identified using one or more instruments. In general, any suitable instrument(s) known in the art for identifying gaseous species of interest can be utilized including, without limitation, mass spectrometers, gas chromatographs, total hydrocarbon analyzers, etc. In this embodiment, analyzer 160 includes a plurality of instruments 161, 162, 163 and a sample collection device 164. Instruments 161, 162, 163 and sample collection device 164 are arranged in parallel such that each receives a representative sample gas from gas outlet 153. In this embodiment, instrument 161 is a mass spectrometer, instrument 162 is a gas chromatograph, and instrument 164 is a total hydrocarbon analyzer. In addition, in this embodiment, sample collection device 164 is a device for periodically (e.g., once an hour, every 30 ft. of lag depth, etc.) capturing and housing separate and discrete samples of the representative sample gas. For example, sample collection device 164 can periodically capture samples of the representative sample gas in separate and distinct sample tubes, which can then be passed off to a third party for independent analysis and identification of the species of interest.

Hot drilling fluid 80e exiting degasser 150 flows into heat exchanger 110 through an inlet 113 and exits heat exchanger 110 through an outlet 114. Within heat exchanger 110, the thermal energy within hot drilling fluid 80e is transferred to cold drilling fluid 80a counterflowing through heat exchanger 110, thereby transitioning hot drilling fluid 80e into a cooled drilling fluid 80g. Accordingly, inlet 113 may also be referred to as hot drilling fluid inlet 113, and outlet 114 may also be referred to as a cooled drilling fluid outlet 114. Cooled drilling fluid 80g flows from outlet 114 of heat exchanger 110 through return line 102 and into return line 72 of circulation system 70. A sample return pump 106 is provided in return line 102 to pull cooled drilling fluid 80g from heat exchanger 110 and pump it through return line 102 to return line 72 of circulation system 70.

In the manner described, samples of drilling fluid are continuously circulated through system 100 and analyzed to identify species of interest therein. In this embodiment, heat exchanger 110 is provided to simultaneously pre-heat the cold drilling fluid 80a supplied to sampling system 100 and cool the hot drilling fluid 80e returned by sampling system 100. This offers the potential to reduce the energy consumption by heater 140, as cold drilling fluid 80a is pre-heated prior to entering heater 140, as well as increase the operating lifetime of return pump 106 by reducing the temperature of hot drilling fluid 80e before it passes therethrough. Cooling the hot drilling fluid 80e with heat exchanger 110 also reduces safety hazards by decreases the total footprint of the hot drilling fluid circuit within sampling system 100.

Sampling system 100 is shown schematically in FIG. 2, however, it is to be understood that the various components of system 100 are coupled together with fluid conduits (e.g., pipes, hoses, or the like) that place the components in fluid communication and allow samples of drilling fluid to be continuously flowed between the various components. For example, supply line 101 comprises a fluid conduit extending from suction tube 103 to supply pump 105 and a fluid conduit extending from supply pump 105 to inlet 111. In addition, a fluid conduit extends from outlet 112 of heat exchanger to inlet 131, and a fluid conduit extends from each outlet 132, 134, 136 to pump 133, pump 135, and inlet 141, respectively. Further, a fluid conduit extends from pump 122 to return line 102, a fluid conduit extends from outlet 142 to inlet 152, and a fluid conduit extends from pump 135 to inlet 151. Still further, a fluid conduit extends from each outlet 153, 154 to analyzer 160 and inlet 113, respectively. Moreover, return line 102 comprises a fluid conduit extending from outlet 114 to return pump 106 and a fluid conduit extending from return pump 105 to return line 72.

Figure 3:
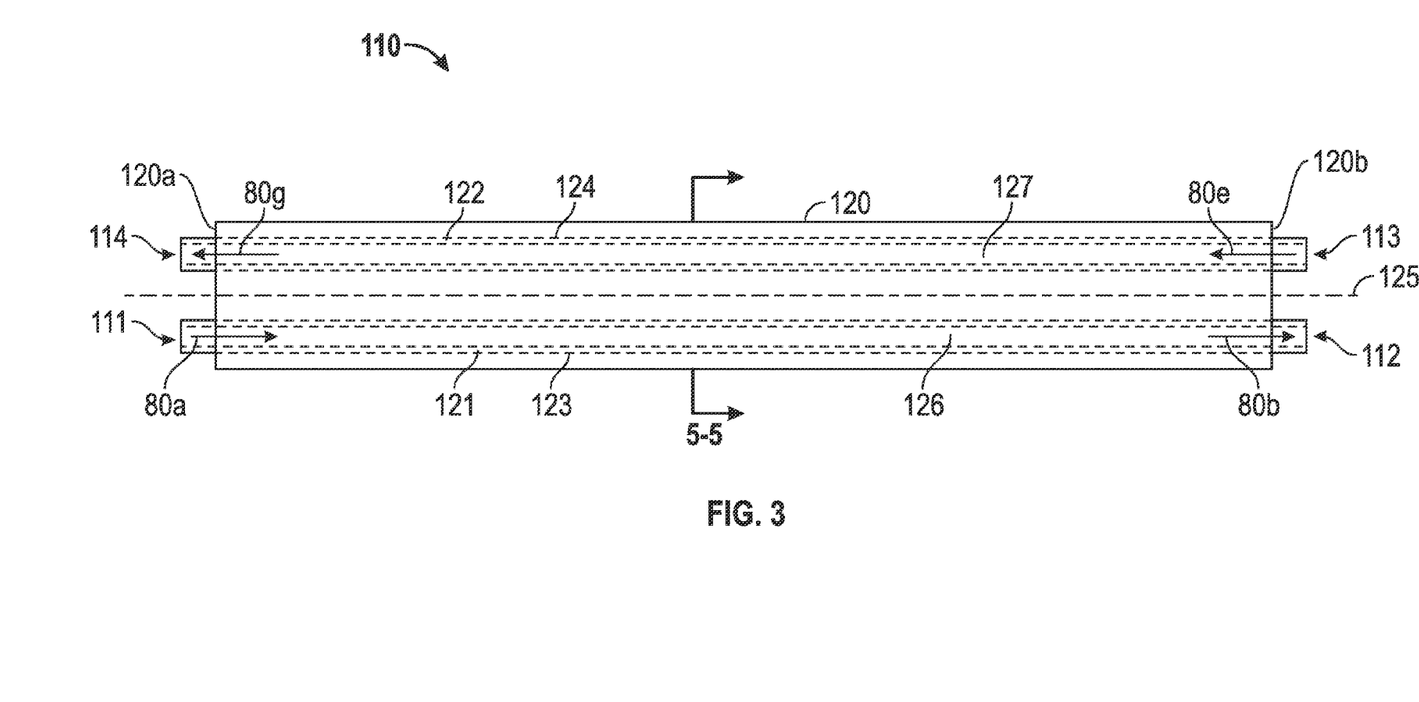
FIG. 3 is a side view of the heat exchanger in the drilling fluid sampling system of FIG. 2.
Figure 4:
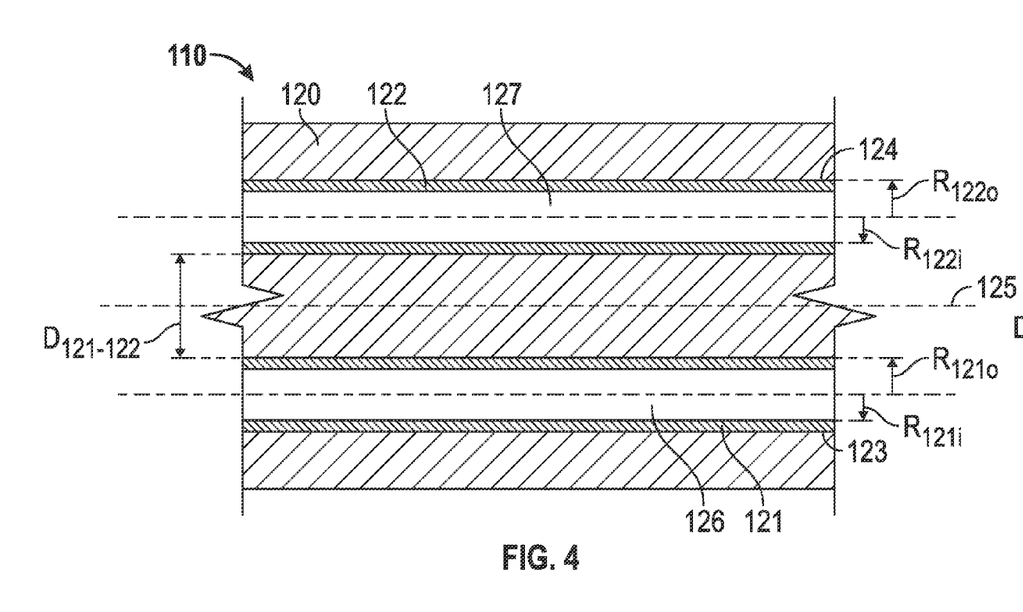
FIG. 4 is a partial longitudinal cross-sectional view of the heat exchanger of FIG. 3.
Figure 5:
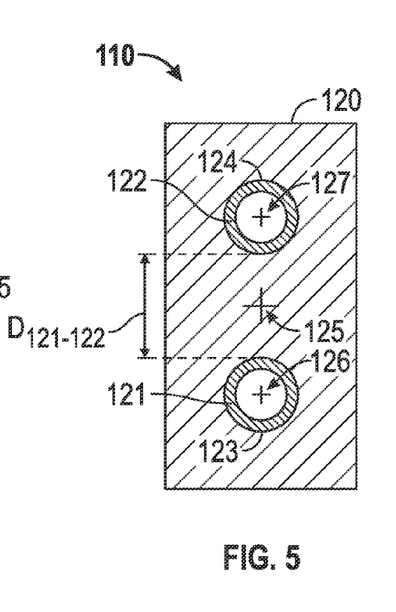
FIG. 5 is a cross-sectional view of the heat exchanger of FIG. 3 taken along section 5-5 of FIG. 3.

Referring now to FIGS. 3-5, in this embodiment, heat exchanger 110 comprises a core or body 120, a first tubular 121 extending through core 120, and a second tubular 122 extending through core 120 extending through core 120 parallel to first tubular 121. In this embodiment, core 120 is an elongate generally solid member having a linear central or longitudinal axis 125, a first end 120a, and a second end 120b opposite end 120a. In addition, core 120 includes a first through bore 123 extending axially between ends 120a, b, and a second through bore 124 extending axially between ends 120a, b. Bores 123, 124 are parallel to axis 125. As best shown in FIG. 5, in this embodiment, core 120 has a rectangular cross-section taken perpendicular to axis 125. However, in general, the core (e.g., core 120) can have any cross-sectional geometry including, without limitation, circular, oval, triangular, square, etc.

Referring again to FIGS. 3-5, tubulars 121, 122 extend axially through core 120 between ends 120a, b. In particular, tubular 121 is coaxially disposed within bore 123 and tubular 122 is coaxially disposed within bore 124. Thus, tubulars 121, 122 are oriented parallel to axis 125 in this embodiment. Although core 120 is an elongate linear member in this embodiment, and bores 123, 124 and corresponding tubulars 121, 122 are parallel and extend linearly between ends 120a, b in this embodiment, in other embodiments, the core (e.g., core 120), the bores (e.g., bores 123, 124), and associated tubulars (e.g., tubulars 121, 122) can have other geometries. However, in general, the bores and the associated tubulars are preferably spaced apart and oriented parallel to each other as they extend through the core. In one exemplary embodiment, the core is a cylindrical block and the bores (with the tubulars disposed therein) extend helically and parallel to teach other through the core.

In this embodiment, each tubular 121, 122 is cylindrical, and has an outer radius $R_{121o}$, $R_{122o}$, respectively, and an inner radius $R_{121i}$, $R_{122i}$, respectively. Outer radius $R_{121o}$ is the same as the radius of bore 123, and radius $R_{122o}$ is the same as the radius of bore 124. Thus, the outer cylindrical surfaces of tubulars 121, 122 contact and engage core 120 along the entire length of core 120. In other words, core 120 completely surrounds each tubular 121, 122. Further, solid core 120 extends between tubulars 121, 122, and thus, there are no voids, gaps, or flow passages between tubulars 121, 122. This enables the direct conduction of thermal energy through core 120 between tubulars 121, 122. The inner radius $R_{121i}$, $R_{122i}$ of each tubular 121, 122, respectively, is preferably between 0.25 in. and 2.0 in., and more preferably 0.5 in. For most drilling operations, the shortest distance $D_{121\text{-}122}$ between tubulars 121, 122 is preferably greater than or equal to the inner diameter of tubulars 121, 122 (i.e., twice the radius $R_{121i}$, $R_{122i}$), and less than or equal to three times the inner diameter of tubulars 121, 122 (i.e., six times the radius $R_{121i}$, $R_{122i}$). For example, if each tubular 121, 122 has an inner radius $R_{121i}$, $R_{122i}$ equal to 0.5 in., then distance $D_{121\text{-}122}$ is preferably greater than or equal to 1.0 in. and less than or equal to 3.0 in. Without being limited by this or any particular theory, these preferred ranges for distance $D_{121\text{-}122}$ offer the potential for efficient heat transfer between tubulars 121, 122 through core 120, while maintaining sufficient strength in core 120.

The radially inner surface of each tubular 121, 122 defines a drilling fluid flow passage 126, 127, respectively. Inlet 111 is provided at one end of flow passage 126 and outlet 112 is provided at the opposite end of flow passage 126. Inlet 113 is provided at one end of flow passage 127 and outlet 114 is provided at the opposite end of flow passage 127. Inlet 111 and outlet 114 are disposed at end 120a of core 120, and inlet 113 and outlet 112 are disposed at end 120b of core 120. Thus, drilling fluid passes through passages 126 in the opposite direction as drilling fluid passes through passage 127. In other words, drilling fluids move counterflow through heat exchanger 110.

Referring still to FIGS. 3-5, core 120 and tubulars 121, 122 are preferably made of rigid materials with a relatively high thermal conductivity (W/m*K) to enhance the conduction of thermal energy from hot drilling fluid 80e flowing through passage 127 to cold drilling fluid 80a flowing through passage 126, thereby simultaneously pre-heating drilling fluid 80a and cooling drilling fluid 80e. Examples of suitable materials for core 120 and tubulars 121, 122 including, without limitation, steel, aluminum, and copper. In this embodiment, core 120 is aluminum that is cast around stainless steel tubulars 121, 122.

In the manner described, heat exchanger 110 allows a metal-to-metal contact between counterflow fluids 80a, 80e, thereby eliminating secondary heat exchange mediums such as oil or water conventionally used in heat exchangers. In addition, heat exchanger 110 does not include any moving parts that are often prone to damage and failure. Eliminating secondary heat exchanges mediums and moving parts offers the potential to enhance durability and simplify maintenance as passages 126, 127 are easily accessed and can be completely cleaned without concern over hidden ports, dead fluid spaces or unused areas that are susceptible to unseen corrosion. The simplistic design for heat exchanger 110 also lends itself well to non-destructive testing and inspection for consistency and reliability purposes, and offers the potential for relatively low cost manufacturing and replacement.

Although drilling fluid circulation system 70 and sampling system 100 are shown in connection with offshore drilling system 10 in FIG. 1, it should be appreciated that circulation system 70 and sampling system 100 can also be used with land-based drilling systems. In addition, although only one heat exchanger 110 is shown in sampling system 100, it should be appreciated that more than one heat exchanger (e.g., heat exchanger 110) can be connected in series to further enhance the transfer of thermal energy between cold drilling fluid 80a and hot drilling fluid 80e.

Figure 6:
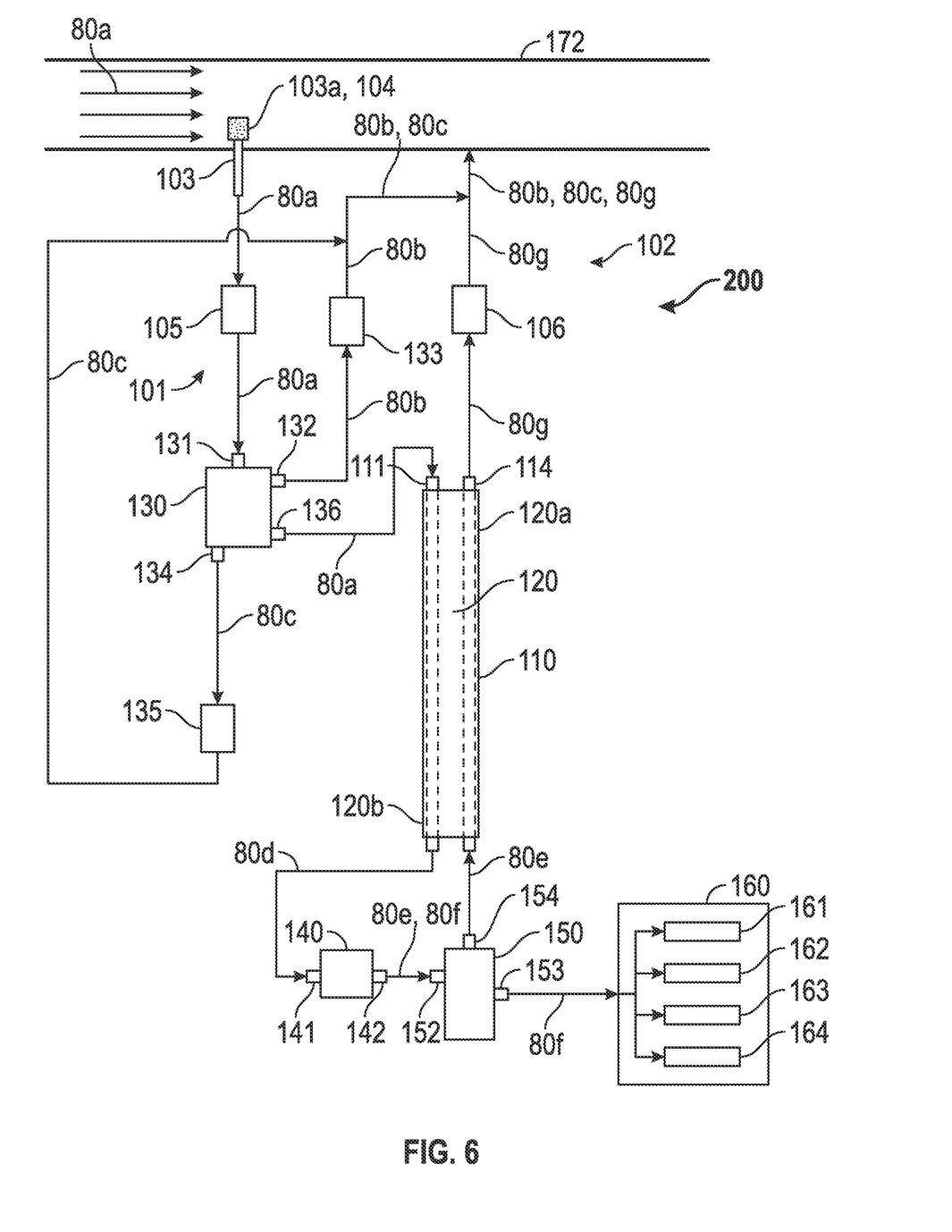
FIG. 6 is a schematic view of an embodiment of a drilling fluid sampling system for use in the drilling system of FIG. 1.

In the embodiment of sampling system 100 described above, separated gases 80c exit phase separator 130 through a separated gas outlet 134, and are pumped to degasser 150 with a de-aerator pump 135. Typically, separated gases 80c include relatively light hydrocarbons that are already in a gaseous state in cold drilling fluid 80a, and thus, are liberated therefrom with relative ease. However, in other embodiments, separated gases 80c are not pumped to degasser 150, but rather, are pumped to sample return line 102. For example, referring now to FIG. 6, an embodiment of a sampling system 200 that can be used in drilling system 10 (e.g., in place of sampling system 100) is shown. Sampling system 200 is the same as sampling system 100 previously described with the exception that separated gases 80c separated from cold drilling fluid 80a in phase separator 130 are pumped to sample return line 102 and not pumped to degasser 150. In particular, separated gases 80c exit phase separator 130 through a separated gas outlet 134, and are pumped with de-aerator pump 135 into sample return line 102, and then pumped through sample return line 102 into drilling fluid return line 72 with return pump 106. Thus, in this embodiment, separated gases 80c are not supplied to degasser 150 and analyzer 160. Rather, in this embodiment, degasser 150 only receives the mixture of hot drilling fluid 80e and gaseous species of interest 80f from heater 140 through inlet 152. Gases 80f are separated from hot drilling fluid 80e within degasser 150, and then exit degasser 150 through gas outlet 153 and flow to analyzer 160 for analysis and identification of species of interest therein. The hot drilling fluid 80e separated from gases 80f exit degasser 150 through outlet 154 and flow to heat exchanger 110.

While preferred embodiments have been shown and described, modifications thereof can be made by one skilled in the art without departing from the scope or teachings herein. The embodiments described herein are exemplary only and are not limiting. Many variations and modifications of the systems, apparatus, and processes described herein are possible and are within the scope of the disclosure. For example, the relative dimensions of various parts, the materials from which the various parts are made, and other parameters can be varied. Accordingly, the scope of protection is not limited to the embodiments described herein, but is only limited by the claims that follow, the scope of which shall include all equivalents of the subject matter of the claims. Unless expressly stated otherwise, the steps in a method claim may be performed in any order. The recitation of identifiers such as (a), (b), (c) or (1), (2), (3) before steps in a method claim are not intended to and do not specify a particular order to the steps, but rather are used to simplify subsequent reference to such steps.

What is claimed is:

1. A system for sampling drilling fluid to identify one or more species of interest within the drilling fluid, the system comprising:
    a heat exchanger including a first fluid passage and a second fluid passage, wherein each fluid passage has an inlet and an outlet;
    a supply line coupled to the inlet of the first fluid passage;
    a return line coupled to the outlet of the second fluid passage;
    a drilling fluid heater having an inlet coupled to the outlet of the first fluid passage and an outlet; and
    a drilling fluid degasser having an inlet coupled to the outlet of the heater, a first outlet coupled to an analyzer configured to identify the one or more species of interest, and a second outlet coupled to the inlet of the second fluid passage.

2. The system of claim 1, wherein the heat exchanger is configured to transfer thermal energy from the samples of drilling fluid flowing through the second fluid passage to the samples of drilling fluid flowing through the first fluid passage.

3. The system of claim 2, wherein the drilling fluid heater is configured to heat the samples of drilling fluid to vaporize or volatize the one or more species of interest.

4. The system of claim 2, wherein the heat exchanger comprises:
    an elongate core having a longitudinal axis, a first end, and a second end;
    a first tubular extending axially through the core from the first end of the core to the second end of the core, wherein the first fluid passage extends through the first tubular; and
    a second tubular extending axially through the core from the first end of the core to the second end of the core, wherein the second fluid passage extends through the second tubular.

5. The system of claim 4, wherein the first tubular has an inner radius, and wherein the first tubular is spaced from the second tubular by a distance greater than or equal to twice the inner radius and less than or equal to six times the inner radius.

6. The system of claim 4, wherein the first tubular and the second tubular each have an inner radius between 0.25 in. and 2.0 in.

7. The system of claim 4, wherein the inlet of the first passage and the outlet of the second passage are each disposed at the first end of the core, and the outlet of the first passage and the inlet of the second passage are each disposed at the second end of the core.

8. The system of claim 4, wherein the core is a solid metal configured to allow conduction of thermal energy directly from the second tubular to the first tubular.

9. The system of claim 8, wherein the core is solid aluminum and each tubular is stainless steel.

10. A method for identifying one or more species of interest in drilling fluid, the method comprising:
    (a) flowing samples of drilling fluid through a heat exchanger;
    (b) pre-heating the acquired samples of drilling fluid in the heat exchanger;
    (c) heating the pre-heated samples of drilling fluid to vaporize or volatize the one or more species of interest within the pre-heated samples of drilling fluid;
    (d) flowing the heated samples of drilling fluid through the heat exchanger; and
    (e) cooling the heated samples of drilling fluid in the heat exchanger.

11. The method of claim 10, wherein (a) comprises flowing the samples of drilling fluid through a first passage in the heat exchanger; and
    wherein (d) comprises flowing the heated samples of drilling fluid through a second fluid passage in the heat exchanger.

12. The method of claim 10, further comprising:
    acquiring the samples of drilling fluid from a return line of a drilling fluid circulation system; and
    returning the cooled sample of drilling fluid to the return line of the drilling fluid circulation system.

13. The method of claim 10, wherein the heat exchanger comprises:
    a solid core;
    a first tubular extending through the core, wherein the first fluid passage extends through the first tubular; and a second tubular extending through the core parallel to the first tubular, wherein the second fluid passage extends through the second tubular.

14. The method of claim 13, wherein the core is solid aluminum and each tubular is stainless steel.

15. The method of claim 10, wherein (b) and (e) occur simultaneously in the heat exchanger by transferring thermal energy from the heated samples of drilling fluid flowing through the second fluid passage to the samples of drilling fluid flowing through the first fluid passage.

16. The method of claim 15, wherein the thermal energy is directly transferred from the heated samples of drilling fluid to the acquired samples of drilling fluid by conduction.

17. The method of claim 15, wherein the thermal energy is transferred exclusively by conduction through one or more metals in the heat exchanger from the heated samples of drilling fluid in the second fluid passage to the samples of drilling fluid in the first fluid passage.

* * * * *